United States Patent [19]
Davis et al.

[11] Patent Number: 5,741,477
[45] Date of Patent: Apr. 21, 1998

[54] NEGATIVE CONTRAST AGENTS FOR MAGNETIC RESONANCE IMAGING COMPRISING BARIUM SULFATE AND A CLAY

[75] Inventors: Michael A. Davis, Westwood, Mass.; Andrew A. Zwarun, Roslyn Heights, N.Y.

[73] Assignee: E-Z-EM, Inc., Westbury, N.Y.

[21] Appl. No.: 545,853

[22] PCT Filed: May 19, 1994

[86] PCT No.: PCT/US94/05604

§ 371 Date: Nov. 13, 1995

§ 102(e) Date: Nov. 13, 1995

[87] PCT Pub. No.: WO94/27499

PCT Pub. Date: Dec. 8, 1994

Related U.S. Application Data

[63] Continuation-in-part of Ser. No. 65,192, May 20, 1993, Pat. No. 5,424,142.

[51] Int. Cl.$^6$ ................................................ A61B 5/055
[52] U.S. Cl. ........................ 424/9.31; 424/684; 424/709; 436/173; 128/653.4; 128/654
[58] Field of Search ........................ 424/9.31, 684, 424/709; 436/173; 128/653.4, 654

[56] References Cited

U.S. PATENT DOCUMENTS

| | | | |
|---|---|---|---|
| 4,010,038 | 3/1977 | Iwasaki et al. | 106/22 |
| 4,126,672 | 11/1978 | Sheth et al. | 424/22 |
| 4,916,170 | 4/1990 | Nambu et al. | 523/137 |
| 5,205,290 | 4/1993 | Unger | 128/653.4 |
| 5,277,896 | 1/1994 | Balkus, Jr. | 424/9 |

Primary Examiner—Gary E. Hollinden
Attorney, Agent, or Firm—McAulay Fisher Nissen Goldberg & Kiel, LLP

[57] ABSTRACT

A negative contrast agent for MRI is an aqueous suspension having a quantity of barium sulfate between 25 and 30 percent by weight and a quantity of bentonite between 2.5 and 3.5 percent by weight in which a substantial portion of the barium sulfate particles have a mean diameter of at least 10 microns. This negative contrast agent provides dark imaging in a T2 weighted pulse sequence; namely a relative signal intensity (RSI) approaching zero. It also provides a relative signal intensity (RSI) of under 30 percent of that of a reference that approximates tissue in a T1 weighted pulse sequence.

12 Claims, 5 Drawing Sheets

FIG. 7 TABLE II

| COMPOSITION | RSI (SE400/20)* |
|---|---|
| 2.5% Bentonite + 0.16 mM Fe + 20% Barium | 0.119 |
| " " + 30% Barium | 0.039 |
| " " + 40% Barium | 0.002 |
| " " + 50% Barium | 0.002 |
| 3.0% Bentonite + 0.16 mM Fe + 15% Barium | 0.157 |
| " " +20% Barium | 0.099 |
| " " +30% Barium | 0.039 |
| " " +40% Barium | 0.010 |

\* These are all points on the curve 54 in FIG. 5. Curve 54 is actually two curves. But the resolution of FIG. 5 does not distinguish between the two curves.

| MATERIAL | RSI (T2) | RSI (T1) |
|---|---|---|
| 25% BaSO$_4$ | 0.285 | 0.793 |
| 3% Bentonite | .004 | 0.800 |
| 0.16 mM Fe | 0.569 | 1.880 |
| 25% BaSO$_4$ + 3% Bentonite | - 0 - | 0.220 |
| 25% BaSO$_4$ + 0.16 mM Fe | 0.79 | 1.510 |
| 3% Bentonite + 0.16 mM Fe | .002 | 0.540 |
| 25% BaSO$_4$ + 3% Bentonite + 0.16 mM Fe | - 0 - | 0.099 |

FIG. 8

NEGATIVE CONTRAST AGENTS FOR MAGNETIC RESONANCE IMAGING COMPRISING BARIUM SULFATE AND A CLAY

This application is a 371 of PCT/US94/05604, filed May 19, 1994 which is a continuation-in-part of U.S. patent application Ser. No. 08/065,192 filed in May 20, 1993, now U.S. Pat. No. 5,424,142 issued Jun. 13, 1995 and having the same title as does this application.

BACKGROUND OF THE INVENTION

This invention relates in general to an improved formulation for a negative contrast agent adapted to be used with magnetic resonance imaging (MRI) and more particularly to agents that can be employed in the gastrointestinal (GI) tract.

The use of contrast agents for MRI and, in particular, use of negative oral contrast agents for GI tract identification in MRI are well known. Among the many agents that are known are those that are disclosed in U.S. Pat. No. 4,927,624 (the use of clay); U.S. Pat. No. 4,770,183 (the use of particular-sized superparamagnetic metal oxide particles) and U.S. Pat. No. 5,069,216 (biologically degradable superparamagnetic metal oxides having less than a predetermined average diameter).

In general, applicants understand that the primary uses and many investigations have focused on perflurocarbons and ferrite materials. Although these materials are effective in providing a good contrast, they are relatively expensive and they may pose problems of toxicity.

Barium sulfate (barium) has been tried on at least an experimental basis as have various clays including, most significantly, bentonite. With a concentration of these materials that is acceptable to the patient, the contrast improvement is very limited. In order to get an optimum contrast improvement, the amount and concentration of barium or clay material required is unacceptable. It is not only difficult to ingest but causes an unacceptable amount of constipation.

Accordingly, it is a major purpose of this invention to provide an improved formulation for a negative image contrast agent for use with MRI that will avoid the previously known toxicity, palatability and constipation problems that occur with presently known agents.

It is another related purpose of this invention to provide the above object with an agent that has reasonable cost so as to facilitate its use in as wide a variety of applications as possible.

The U.S. Pat. No. 5,069,216 issued Dec. 3, 1991 provides a fairly extensive discussion of the technology in this art and need not be repeated here. The agents of concern are called negative contrast agents because they serve to decrease the signal intensity thereby resulting in image darkening. More particularly, in MRI the images are produced on the trailing edge of a magnetic pulse when the hydrogen nuclei in tissue provide a signal when switching from an excited magnetized state to a relaxed magnetized state. The switch is called a relaxation switch and the time it takes is called a relaxation time period. Without going into the specific physics of it, there are two relaxation times, called T1 and T2 (respectively longitudinal relaxation time and transverse relaxation time). These two relaxation times T1 and T2 generate two different signals which provide two different images.

Indeed, every pulse sequence generates both T1 and T2 signals in a specific proportion. Those sequences generating substantially more T1 signal are referred to herein as T1 weighted pulse sequences which yield T1 weighted images. The converse applies with respect to those sequences generating a substantially larger T2 signal which yield T2 weighted images.

The image produced often lacks clear definition (contrast) because of comparable signals produced by adjacent tissues other than the organ or tissue of interest. A contrast agent which localizes or concentrates in a tissue serves to modify the magnetic properties of that tissue in which it concentrates and thus can provide a better contrast between that tissue and the surrounding tissue.

Negative contrast agents operate in three different ways to modify the magnetic properties of the tissue in which they are concentrated. These three ways are the following:

A. By increasing the magnetic susceptibility of the tissue. Superparamagnetic agents operate in this way and to a much lesser extent so does barium and clay.

B. By decreasing proton density. This occurs by displacing water. This is how barium, perflurocarbons and gas work.

C. By reducing the rotational mobility of the protons present. This is essentially how the clays work.

It is important to recognize that an optimum contrast agent is one which will provide an appropriate trade-off of three functional characteristics. These three functional characteristics are: (1) marked contrast between the tissue of interest and the surrounding tissue, (2) minimum adverse medical impact on the patient; and (3) acceptable to a patient from the point of view of taste and comfort. An optimum contrast agent is one that does not hold its magnetic state in the absence of an employed magnetic field, is not toxic to the human body and does not require quantities which will cause discomfort such as constipation.

In addition, cost is a major factor in providing an agent which is to be used in a large number of procedures. Thus it is another object of this invention to obtain an optimum trade-off of the above three functional characteristics together with cost as a fourth parameter.

DEFINITIONS

Relaxation Time

This is the time, usually in fractions of a second, in which the hydrogen nucleus switches from an excited magnetized state to a relaxed magnetized state when the magnetic gradient or RF pulse is removed. There is a different relaxation time for the T1 mode and for the T2 mode. The relaxation time in the T1 mode can be as little as 2.2 seconds for a 40 percent by weight of barium sulfate and as little as 0.12 seconds in the T1 mode for 4% by weight of bentonite. The relaxation time in the T2 mode can range from 0.4 seconds for a 10 percent barium sulfate solution to 0.05 seconds for a 5 percent bentonite solution. Relaxation time has a significant relationship to the signal intensity. However, that relationship is quite complex.

T1 Weighted and T2 Weighted Modes

This terminology is known in the art and will not be explicated in detail here because of its complexity. This disclosure indicates the particular pulse sequence that was used in the T1 mode and T2 mode. Specifically, a known pulse sequence that is designated in the art as SE400/20 is a pulse sequence used for the T1 weighted mode and a known pulse sequence SE1500/50 was employed when testing response in the T2 weighted mode.

Relative Signal Intensity (RSI)

To apprise the value of the contrast agent, it must be compared against a standard. One standard can be pure water. Another standard commonly used in the art is a copper sulfate ($CuSO_4$) solution at a concentration that provides a signal response that approximates the signal intensity of body tissue. The signal intensity of various substances, barium sulfate, bentonite or ferrite are measured relative to the standard used. The materials considered as a negative contrast agent provide a signal intensity response substantially less than that of the standard and thus can be compared with the standard by designating what fraction of signal intensity they provide compared to that of the standard. Thus relative signal intensity for a negative contrast agent is less than 1.0. In the case of certain barium sulfate compositions, the RSI can be greater than 1.0. But RSI is the key figure of merit for measuring the negative contrast agents. The lower the RSI, the better the negative contrast. It should be noted that the RSI has to be measured in response to both the T1 weighted signal as well as in response to the T2 weighted signal.

Barium

In this field, barium sulfate ($BaSO_4$) is often referred to as barium. This convention will be frequently followed herein and any reference to "barium" should be understood to mean barium sulfate.

Particle Size

It should be understood that reference to a particle size herein is to a mean particle size and that the distribution of particle sizes is substantial in commercially available bariums. For example, a commercially available barium having a mean particle size of ten microns would normally have particle sizes that range from three microns to forty or even fifty microns and would also have a fairly broad standard deviation.

Percent By Weight

All weight percentages employed herein are the weight of the constituent involved as a percentage of the total weight of the suspension. This is sometimes referred to as weight/weight in order to distinguish from weight/volume. Accordingly, an indication herein that the clay involved in the suspension is 3% by weight bentonite, means that 3% of the total weight of the suspension is the weight of the bentonite in the suspension.

Contrast Agent/Bowel Marker

Although the agent of this invention is called a contrast agent and in particular negative contrast agent, that terminology is often used to refer to agents which directly affect the signal intensity of the region of interest. By contrast, the agent of this invention is used to darken the bowel (that is to reduce the MRI signal from the bowel) so as to avoid confounding the image from the region of interest. Thus strictly speaking the agent of this invention might be more properly termed a bowel marker rather than a contrast agent. However, for convenience it is referred to herein as a contrast agent with the understanding expressed above.

BRIEF DESCRIPTION

What applicant has determined is that particular combinations of known negative contrast agents provide an enhanced result which permits the use of sufficiently smaller amounts of the constituents so as to meet the objectives of this invention.

More particularly, an amount of barium sulfate (barium) acceptable to the patient containing a relatively small percentage of bentonite provides an effective darkening (negative) contrast agent in various spin echo and gradient echo pulse sequences. The barium concentration required is approximately half of that required without the bentonite.

One fairly optimum formulation, based on non-human testing, is an aqueous suspension having 25 to 30 percent by weight of barium sulfate particle, 2.5 to 3.0 percent by weight of bentonite and in which the barium particles have a mean diameter of ten microns or more.

However, it is believed that a range of barium from 20 to 40 percent by weight can be useful with bentonite having a range of between 2.0 and 4.0 percent by weight.

THE FIGURES

FIG. 1 is a graph representing the relative signal intensity (RSI) of the spin echo pulse sequence modes T1, T2 and proton density as a function of the ratio between ten micron barium and one micron barium. The ordinate (y-axis) shows relative signal intensity. The abscissa (x-axis) shows the weight of the ten micron barium in the suspension. It has to be kept in mind that each test is of an agent which is 25% by weight by barium. However, each agent is a mixture of one micron barium and ten micron barium. The abscissa indicates how much of that total barium is ten micron barium. Accordingly, the right most point on the abscissa represents a suspension which is 25% by weight of ten micron barium and does not contain any one micron barium. The measurement where the abscissa is zero is one where the suspension is 25% by weight one micron barium and does not contain ten micron barium. The suspension contains three percent by weight bentonite.

Figure 6:
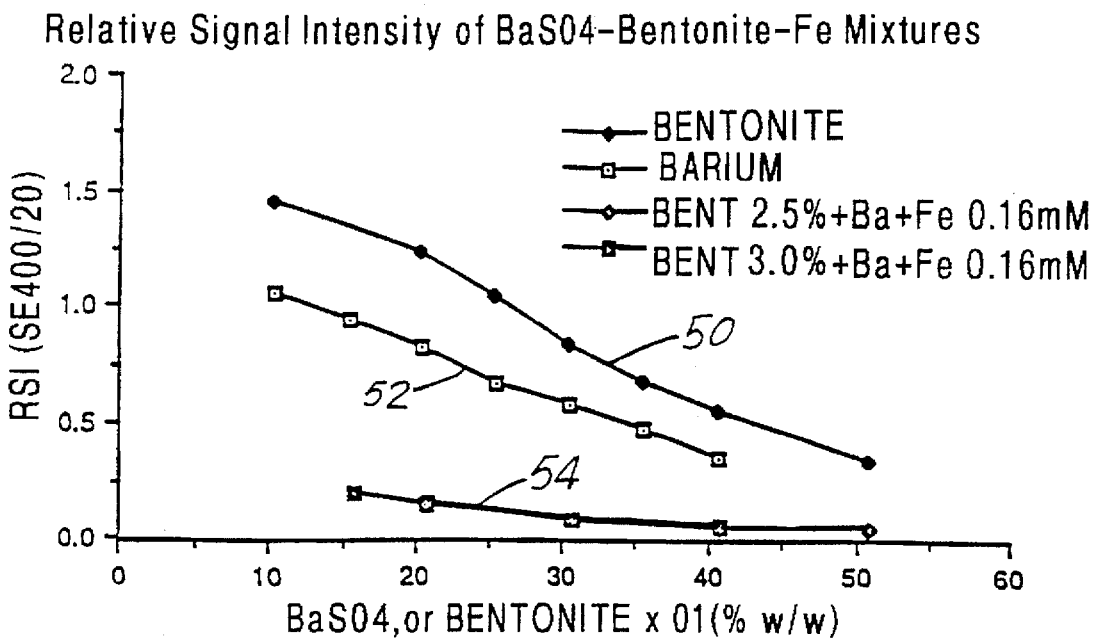

FIG. 6 is a graph showing the relative signal intensity (RSI) in response to a typical T1 weighted pulse sequence for a typical barium (curve 50), bentonite (curve 52) and two compositions (curve 54) wherein a ferrite was added.

FIG. 7 is a table designated as Table II. It provides the specific data from which curve 54 of FIG. 6 is plotted. The RSI numbers in Table II are taken from lab measurements. The standard deviation is appreciable so that an RSI measurement of 0.002 has a measurement error that makes it comparable to the 0.010 measurement. The numbers represent present measurements and will require refinement. The resultant curves indicate tendencies and direction only.

FIG. 8 is a table designated as Table III. It is a table contrasting RSI responses in T1 and T2 weighted modes of various compositions. Table III provides a comparison of RSI response for individual constituents and for mixtures of this invention. These numbers also represent averages having a substantial standard deviation and provide an indication of how various compositions compare.

DESCRIPTION OF THE PREFERRED EMBODIMENTS

It has been found that a combination of barium sulfate particles together with an appropriate pharmaceutically acceptable clay in aqueous suspension will produce a negative contrast agent which provides a lower relative signal intensity (RSI) than would be expected from the additive effects of the two constituents.

In particular, this combination permits the use of sufficiently low amounts of barium (for example, 25% by weight) sufficiently low amounts of clay (for example, 3% by weight) so that the adverse effects on the human patient (in particular, discomfort and constipation) are minimized.

Most particular, a smectite clay of the type known as bentonite has been found particularly useful in weight quantities as low as three percent. But this three percent by weight of bentonite is useful in combination with a substantial amount of barium. What has further been found is that the larger the particle size of the barium, consistent with keeping the barium in suspension, the more effective is the barium in combination with the bentonite to minimize the relative signal intensity and therefore provide an effective negative contrast agent.

What has been found is that a given weight of barium having a particle size of approximately ten microns provides a lower signal intensity ratio than where the particle size is smaller.

Accordingly, the presently preferred negative contrast agent is a water suspension having (a) at least 25 percent by weight barium of approximately ten micron mean diameter and (b) at least three percent by weight of bentonite. Such an agent has been found to give a T2 signal intensity ratio of approximately 0.1, a T1 signal intensity ratio of between 0.3 and 0.35 and a proton density ratio of approximately 0.4 to 0.45. These three parameters are for spin echo pulse sequences.

FIGS. 1 through 4 and Table I illustrate some of the detailed test results that lead to the above conclusions.

FIGS. 1 through 4 represent tests using four different bases that are used with radiological barium mixtures. Accordingly, these four bases contain known gums or suspending agents typical of those used in connection with barium sulfate compositions in use today for radiological purposes. What is significant about these four results is how similar they are in spite of the fact the bases varied. One conclusion from these results is that a predetermined combination of barium by weight and particle size with bentonite by weight will provide a predetermined RSI. A further conclusion is that the larger the barium particle size, the more effective will a given weight of barium be in a composition for the purposes of this invention.

One somewhat unexpected result is that the smaller particle size barium is less effective than the larger particle size barium even though the smaller the particle the greater the surface area of the particle for a given weight of barium. It is not understood why this is the case. However it is noted that when bentonite is omitted from the agent B (ten micron) formulation, the test results were varied, ranging from RSI values greater than one for the T2 mode in some mixtures to RSI values as low as 0.1 for the T1 mode in other mixtures.

As is known in the art, a barium which has a mean particle size of ten microns includes particle sizes that may range from three microns to forty or even fifty microns. In addition, the standard deviation of the particle size of barium products which are available in the marketplace is broad. Nonetheless, for a given percentage weight of barium, it has been found that the larger particle size, if maintained in suspension, provides, in the mixture of this invention, the lower signal intensity ratio.

It is known that the lower the relative signal intensity (RSI) in the gastro-intestinal tract, the better will be the contrast with surrounding tissue and this will better enable the doctor to make an effective diagnosis. The gastro-intestinal tract, poses a particular problem that calls for as low a relative signal intensity as possible. The gastro-intestinal tract because of peristalsis, is always moving. This movement creates an artifact in the adjacent signal that is due to motion. A low signal from the gastro-intestinal tract will minimize this motion artifact.

The FIGS. 1 through 4 and Table II data are parameters in the spin echo mode. Tests show that there is also advantage from a negative contrast point of view in gradient echo pulse mode. Although the improvement in gradient echo mode is not as great as in spin echo mode, it is still an improvement which further enhances the value of the agent of this invention.

The addition of ferrite to certain combinations of barium and bentonite has been found to provide a further improvement. However, it has also been found that ferrite is not necessary to obtain the desired negative contrast agent, especially if the barium is selected with regard to its particle size.

Figure 1:
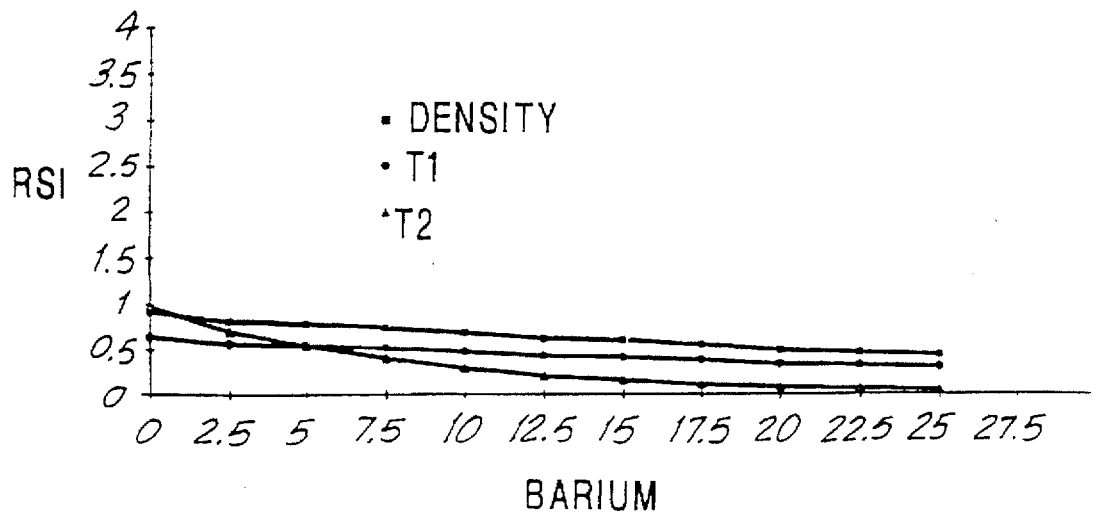
Figure 2:
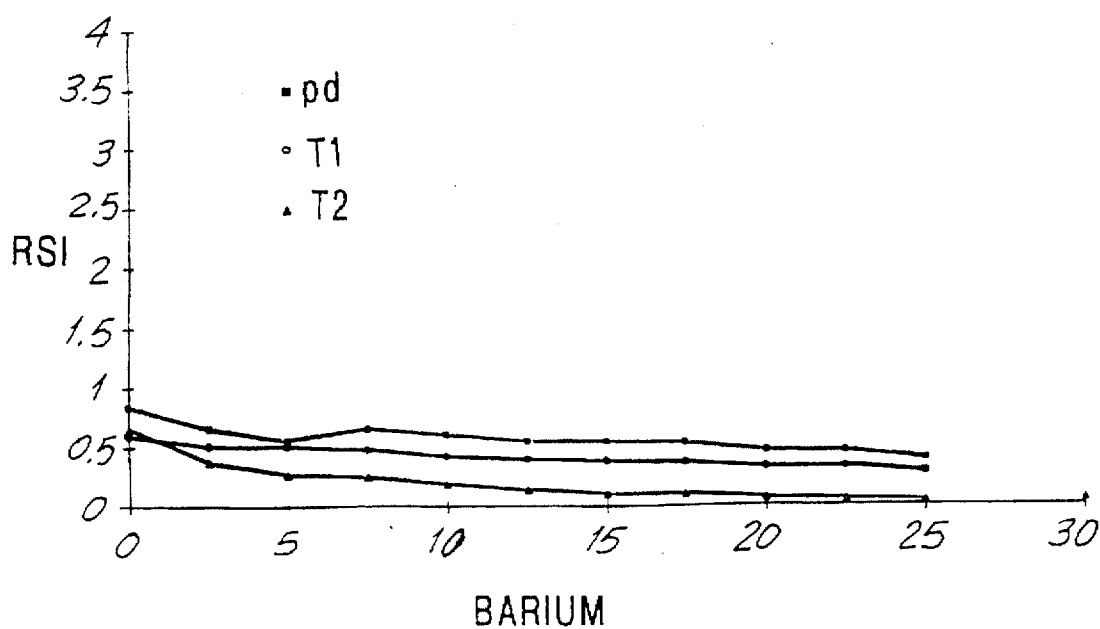
FIG. 2 is a graph like FIG. 1 except that a different standard gum suspension agent was used.
Figure 3:
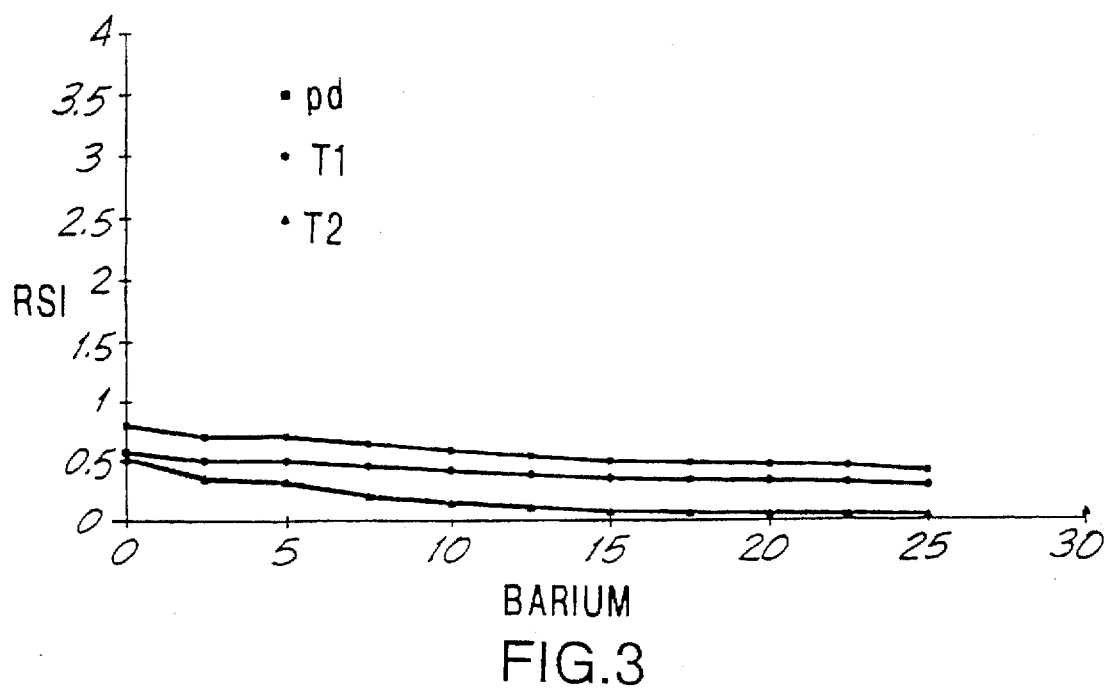
FIG. 3 is a graph like FIGS. 1 and 2 except that a third standard gum suspension agent was used.
Figure 4:
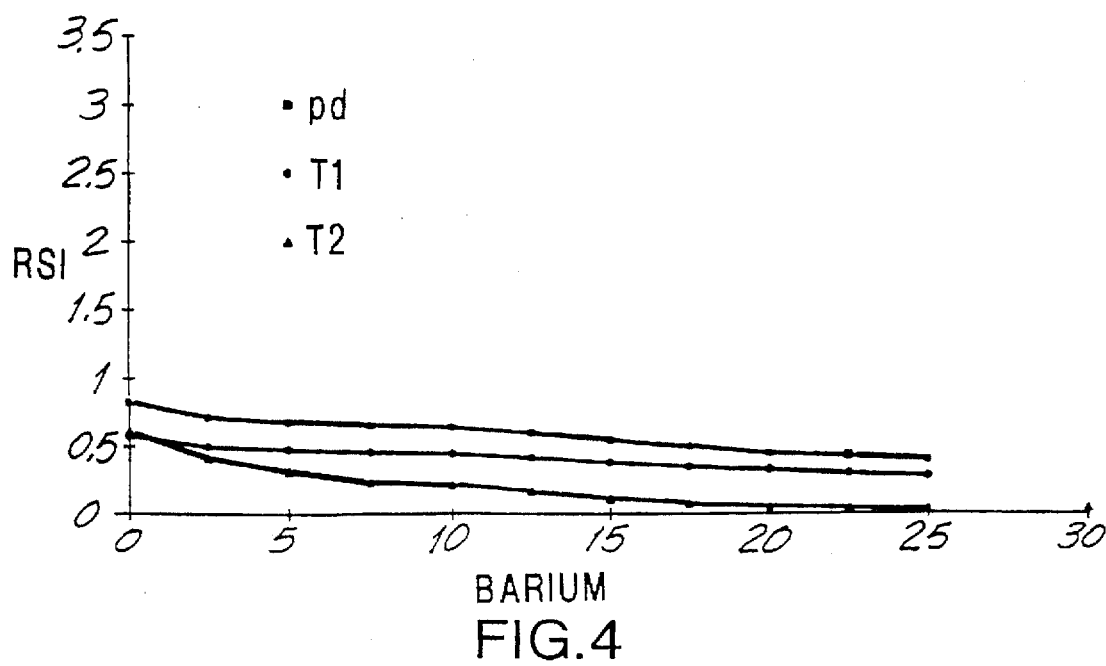
FIG. 4 is a graph like those of FIGS. 1, 2 and 3 except that a fourth standard gum suspension agent was used.
Figure 5:
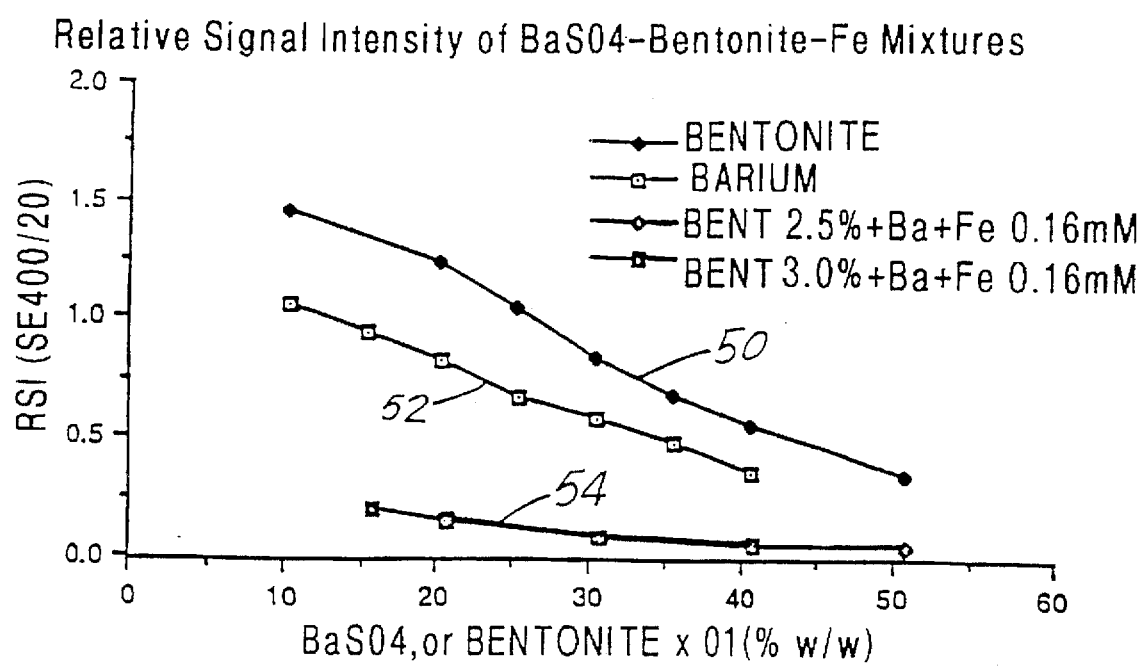
FIG. 5 is a table designated as Table I. It indicates the average value, for the three spin echo pulse sequence modes involved, of the two extreme points on the four graphs shown in FIGS. 1 through 4.

FIG. 5 is an instructive curve to illustrate the relative signal intensity (RSI relative to water) for a very typical T1 pulse sequence SE400/20 for bentonite, curve 50; barium, curve 52 and two formulations employing a ferrite, curve 54. The two formulations produce overlapping curves. Table II, associated with FIG. 5, lists the values experimentally obtained that are used to generate the curve 54.

More particularly, curve 50 shows that the RSI for bentonite ranges from 1.5 where the bentonite concentration is one percent by weight to approximately 0.35 when the bentonite is five percent by weight in a water carrier. The numbers on the X-axis in FIG. 1 have to be divided by ten to provide the bentonite weight percent values.

Curve 52 shows that for barium sulfate, the RSI ranges from approximately 1.0 at a ten percent by weight of barium in a water carrier to an RSI of approximately 0.35 with a forty percent by weight of barium.

Curve 54 shows that when bentonite is anywhere between 2.5 percent to 3.0 percent by weight and ferrites are at 0.16 millimolar (mM) then the RSI ranges from approximately 0.16 at fifteen percent by weight of barium to approximately 0.002 when barium is as high as forty percent by weight.

Because the higher values of barium are not acceptable to a patient, a usable embodiment will employ barium somewhere between twenty-five and thirty percent by weight.

It should be noted that FIG. 5 illustrates RSI for the T1 mode. When bentonite is over two percent by weight, the RSI for the T2 mode is essentially zero; where water is the standard. It should be noted that the ferrite at 0.16 millimolar (mM) by itself provides an RSI of close to two; meaning that the signal it would generate would be twice as strong as that of water.

As shown in Table III, the three percent level of bentonite greatly reduces T2 mode signal in all combinations; where water is the standard. However, the RSI for the T1 mode is as high as 80 percent (0.8) with a twenty-five percent barium composition and as high as 80 percent with a three percent bentonite composition. Combining twenty-five percent barium and three percent bentonite provides an RSI for the T1 mode of about twenty percent (0.2). It should be noted that 0.16 millimolar (mM) ferrite provides a T1 substantially greater than that of water. Combining that amount of ferrite with barium increases the RSI from 80 percent to 150 percent. Combining that amount of ferrite with bentonite decreases the RSI modestly from 80 percent to 60 percent.

But, combining that amount of ferrite with the barium and bentonite combination cuts the RSI in half from 20 percent to 10 percent.

The RSI results shown in Table III show that 0.16 mM ferrite has a substantial RSI by itself and indeed, when added to barium or bentonite, will either increase the RSI or change it very little. Yet, it has been found that a larger quantity of ferrite will have the effect of reducing the RSI in the T1 mode quite substantially. For example, if the amount of ferrite is 1.0 mM, the RSI for the T1 mode can be reduced to essentially zero. However, because of the cost factor this amount of ferrite is impractical. However, the ferrite can be reduced substantially to approximately 0.5 mM or less when in combination with appropriate amounts of barium and bentonite to provide an RSI even less than that of the last line on Table III.

A number of different barium sulfate compositions have been tested to determine the different effects they have on RSI. Commercially available barium compositions used alone have an RSI in the T1 weighted mode that range from approximately 0.3 to over 1.0 using water as the reference. It is not understood as to what it is about these commercially available barium sulfate constituents that affects their response in the T1 weighted mode.

The test results shown in FIGS. 1 through 4 suggest that particle size makes a difference, at least in combination with bentonite. Various examinations of the barium compositions used alone have shown no clear relationship between particle size and RSI. The barium compositions used alone and the barium plus bentonite compositions used to provide the results shown in FIGS. 1-4 all contain standard gums such as xanthan and tragacanth to act as emulsifying agents which aid in keeping the barium particles in suspension.

What is claimed is:

1. A negative contrast agent used in magnetic resonance imaging of the gastrointestinal tract comprising:

a suspension having a substantial portion of a first constituent consisting of barium sulfate particles and a substantial portion of a second constituent comprising particles selected from at least one of the group of materials consisting of pharmaceutically acceptable clays, said second constituent constituting at least two percent by weight of said suspension, a substantial portion of said barium sulfate particles having a mean diameter sufficiently large to provide a relative signal intensity substantially less than 0.5 in at least one of the MRI pulse sequence modes.

2. The negative contrast agent of claim 1 wherein said mean diameter of said portion of said barium sulfate particles is at least ten microns.

3. The negative contrast agent of claim 1 wherein said second constituent is a smectite clay.

4. The negative contrast agent of claim 2 wherein said second constituent is a smectite clay.

5. The negative contrast agent of claim 1 wherein said second constituent constitutes at least two percent by weight of said suspension.

6. The negative contrast agent of claim 2 wherein said second constituent constitutes at least two percent by weight of said suspension.

7. The negative contrast agent of claim 1 wherein at least ten percent by weight of said suspension is constituted by barium sulfate particles having a mean diameter of at least ten microns.

8. The negative contrast agent of claim 2 wherein at least fifteen percent by weight of said suspension is constituted by barium sulfate particles having a mean diameter of at least ten microns.

9. The negative contrast agent of claim 1 wherein at least twenty-five percent by weight of said suspension is constituted by barium sulfate particles having a mean diameter of at least ten microns.

10. The negative contrast agent of claim 7 wherein said second constituent constitutes at least two percent by weight of said suspension.

11. The negative contrast agent of claim 8 wherein said second constituent constitutes at least two percent by weight of said suspension.

12. The negative contrast agent of claim 9 wherein said second constituent constitutes at least two percent by weight of said suspension.

* * * * *